United States Patent
Sakamoto (10) Patent No.: US 11,679,269 B2
(45) Date of Patent: *Jun. 20, 2023

(54) DEFIBRILLATION CATHETER SYSTEM, DEFIBRILLATION POWER SUPPLY DEVICE AND METHOD FOR CONTROLLING DEFIBRILLATION POWER SUPPLY DEVICE

(71) Applicant: KANEKA CORPORATION, Osaka (JP)

(72) Inventor: Shinichiro Sakamoto, Settsu (JP)

(73) Assignee: KANEKA CORPORATION, Osaka (JP)

( * ) Notice: Subject to any disclaimer, the term of this patent is extended or adjusted under 35 U.S.C. 154(b) by 63 days.

This patent is subject to a terminal disclaimer.

(21) Appl. No.: 16/986,591

(22) Filed: Aug. 6, 2020

(65) Prior Publication Data

US 2020/0360705 A1    Nov. 19, 2020

Related U.S. Application Data

(63) Continuation of application No. PCT/JP2019/002979, filed on Jan. 29, 2019.

(30) Foreign Application Priority Data

Feb. 7, 2018   (JP) .............................. JP2018-020530

(51) Int. Cl.
*A61N 1/39*    (2006.01)
*A61N 1/05*    (2006.01)

(52) U.S. Cl.
CPC ......... *A61N 1/3956* (2013.01); *A61N 1/0563* (2013.01); *A61N 1/3912* (2013.01);
(Continued)

(58) Field of Classification Search
CPC .. A61N 1/0563; A61N 1/3918; A61N 1/3931; A61N 1/3975
See application file for complete search history.

(56) References Cited

U.S. PATENT DOCUMENTS 4,077,413 A    3/1978  Partridge
5,285,779 A *  2/1994  Cameron ............. A61N 1/3925
                                                  320/166
(Continued)

FOREIGN PATENT DOCUMENTS

JP    2010-220778 A    10/2010
JP    2017-176349 A    10/2017

OTHER PUBLICATIONS

International Search Report (PCT/ISA/210) issued in PCT/JP2019/002979 dated Apr. 2, 2019.

*Primary Examiner* — Eric D. Bertram
(74) *Attorney, Agent, or Firm* — Birch, Stewart, Kolasch & Birch, LLP (57) ABSTRACT

Provided are a defibrillation catheter system, a defibrillation power supply device, and a method for controlling the device during observation of intracardiac potential and defibrillation. A defibrillation catheter system 1 includes a catheter 20; a first power supply part 6A and a second power supply part 6B connected to the catheter 20; and an electrocardiograph 40 measuring an intracardiac potential, wherein the catheter 20 is provided with a first electrode group 21 having at least a 1-1 electrode and a 1-2 electrode and a second electrode group 22 having at least a 2-1 electrode and a 2-2 electrode, the first and second electrode groups 21 and 22 are connected to the electrocardiograph 40, the 1-1 electrode and the 2-1 electrode are connected to the first power supply part 6A, and the 1-2 electrode and the 2-2 electrode are connected to the second power supply part 6B.

9 Claims, 5 Drawing Sheets

(52) U.S. Cl.
CPC ......... *A61N 1/3918* (2013.01); *A61N 1/3931* (2013.01); *A61N 1/3937* (2013.01); *A61N 1/3975* (2013.01)

(56) References Cited

U.S. PATENT DOCUMENTS

| | | | |
|---|---|---|---|
| 5,522,850 A | | 6/1996 | Yomtov et al. |
| 5,757,167 A | * | 5/1998 | Arora ........................ G05F 1/59 323/224 |
| 6,016,446 A | * | 1/2000 | Belalcazar ........... A61N 1/3704 607/9 |
| 2009/0036943 A1 | * | 2/2009 | Signoff .................. A61N 1/378 607/36 |
| 2010/0114215 A1 | * | 5/2010 | Burnes ............... A61N 1/39624 607/34 |
| 2011/0319948 A1 | * | 12/2011 | Onodera .............. A61N 1/0563 607/5 |

\* cited by examiner

DEFIBRILLATION CATHETER SYSTEM, DEFIBRILLATION POWER SUPPLY DEVICE AND METHOD FOR CONTROLLING DEFIBRILLATION POWER SUPPLY DEVICE

CROSS REFERENCE TO RELATED APPLICATIONS

This application is a Continuation of PCT International Application No. PCT/JP2019/002979, filed on Jan. 29, 2019, which claims priority under 35 U.S.C. 119(a) to Patent Application No. 2018-020530, filed in Japan on Feb. 7, 2018, all of which are hereby expressly incorporated by reference into the present application.

TECHNICAL FIELD

The present invention relates to a catheter system for performing defibrillation, a defibrillation power supply device for, for example, generating a voltage waveform to be applied during defibrillation and selecting an electrode to which a voltage is applied, and a method for controlling the device.

BACKGROUND ART

In the treatment of arrhythmia such as atrial fibrillation or ventricular fibrillation, defibrillation is performed to restore the heart rhythm to normal by applying electrical stimulation. For the defibrillation, an automated external defibrillator (AED), an implantable cardioverter defibrillator (ICD), a defibrillation paddle system, and a defibrillation catheter system are used. In particular, the defibrillation catheter system can measure an intracardiac potential using an electrode provided on the surface of the catheter, while directly applying electrical stimulation to the heart through the electrode. In addition, the defibrillation catheter system is advantageous in that it can use a voltage waveform with lower energy than the external defibrillator, by which the burden on a patient is reduced. The defibrillation catheter system is also advantageous in that it can also be used during ablation and cardiac catheterization for diagnosis of arrhythmia.

In the treatment of atrial fibrillation, it is necessary to apply a voltage during an absolute refractory period so that the ventricular muscles do not respond. If stimulation is applied during periods other than the absolute refractory period, ventricular muscles may respond to cause ventricular fibrillation. Therefore, in the defibrillation catheter system, it is necessary to apply the voltage in synchronization with the R wave.

As an example of such a defibrillation catheter system, Patent Document 1 discloses a catheter system including a defibrillation catheter, a power supply device for applying a DC voltage to electrodes of the catheter, and an electrocardiograph. This system uses a changeover switch with one circuit and two contacts to switch between defibrillation and measurement of intracardiac potential. Therefore, this system cannot unfortunately acquire the intracardiac potential during charging of energy to be delivered for defibrillation and during defibrillation.

In view of this, a system capable of measuring an intracardiac potential during execution of intracardiac defibrillation has been developed. For example, Patent Document 2 discloses, during intracardiac defibrillation, connecting some (RA electrode and CS electrode) of electrodes of an electrode catheter to an electrocardiograph through a protective resistance, instead of completely cutting off the connection between the electrocardiograph and the electrode catheter.

RELATED ART DOCUMENTS

Patent Documents

Patent Document 1: JP2010-220778A
Patent Document 2: JP2017-176349A

SUMMARY OF THE INVENTION

Technical Problem

In the intracardiac defibrillation system disclosed in Patent Document 2, during intracardiac defibrillation in which an on-off switch is in off state, an intracardiac potential signal is transferred to the electrocardiograph through the protective resistance having a relatively large resistance value, so that an intracardiac electrographic waveform displayed in the electrocardiograph is damped more than that during intracardiac electrocardiographic measurement where the on-off switch is in on state. In addition, during intracardiac defibrillation, an electrode catheter short switch is in a short state, so that one measured potential is obtained by averaging the potentials of the eight RA electrodes, and one measured potential is obtained by averaging the potentials of the eight CS electrodes. Therefore, the electrocardiogram of the RA electrodes and the CS electrodes has a rounding waveform as compared with that during the intracardiac electrocardiographic measurement, and the intracardiac potential cannot independently be acquired at each electrode. Furthermore, independent on-off switches are each required for eight CS electrodes and eight RA electrodes, which may increase the circuit scale and require complex control. In view of this, an object of the present invention is to provide a defibrillation catheter system, a defibrillation power supply device, and a method for controlling the device that enable observation of intracardiac potential even during defibrillation in the same manner as during intracardiac electrocardiographic measurement, and that can be easily controlled.

Solutions to the Problems

The gist of a defibrillation catheter system according to the present invention that can overcome the above problems is as follows. A defibrillation catheter system includes a catheter extending in a longitudinal direction, a first power supply part for generating a voltage to be applied to the catheter, the first power supply part connected to the catheter, a second power supply part for generating a voltage to be applied to the catheter, the second power supply part connected to the catheter, and an electrocardiograph for measuring an intracardiac potential. The catheter is provided with, on a distal side, a first electrode group having at least a 1-1 electrode and a 1-2 electrode and a second electrode group having at least a 2-1 electrode and a 2-2 electrode, the second electrode group being disposed closer to a proximal side than the first electrode group. The first electrode group and the second electrode group are connected to the electrocardiograph without a switching part, the 1-1 electrode and the 2-1 electrode are connected to the first power supply part, and the 1-2 electrode and the 2-2 electrode are connected to the second power supply part. As described above, in the defibrillation catheter system according to the present invention, the first electrode group and the second electrode group are connected to the electrocardiograph without a switching part, whereby the first electrode group and the second electrode group are constantly connected to the electrocardiograph. Therefore, the intracardiac potential can be measured by each electrode even during defibrillation.

In the defibrillation catheter system, the first power supply part is preferably connected to the 1-1 electrode and the 2-1 electrode but not to the 1-2 electrode and the 2-2 electrode, and the second power supply part is preferably connected to the 1-2 electrode and the 2-2 electrode but not to the 1-1 electrode and the 2-1 electrode.

The defibrillation catheter system preferably includes three or more power supply parts including the first power supply part and the second power supply part, and the number of the power supply parts is preferably equal to the number of the electrodes in the first electrode group.

The defibrillation catheter system preferably further includes a synchronization circuit for synchronizing timings of applying a voltage to the 1-1 electrode and the 2-1 electrode, and applying a voltage to the 1-2 electrode and the 2-2 electrode, the synchronization circuit being connected to the first power supply part and the second power supply part.

The defibrillation catheter system preferably further includes a resistance of 200Ω or less, the resistance being provided between the first power supply part and the electrocardiograph and/or between the second power supply part and the electrocardiograph.

The defibrillation catheter system may include an overvoltage protection circuit for protecting the electrocardiograph from an overvoltage, the overvoltage protection circuit being provided between the first power supply part and the electrocardiograph and/or between the second power supply part and the electrocardiograph.

The defibrillation catheter system preferably further includes an impedance measuring circuit for measuring an impedance between the 1-1 electrode and the 2-1 electrode, the impedance measuring circuit being connected between the 1-1 electrode and the 2-1 electrode, wherein the 1-1 electrode is preferably connected to the impedance measuring circuit through a first switch, and the 2-1 electrode is preferably connected to the impedance measuring circuit through a second switch.

The defibrillation catheter system preferably further includes a third electrode group including electrodes provided between the first electrode group and the second electrode group in the longitudinal direction of the catheter, the third electrode group being used to measure the intracardiac potential.

The defibrillation catheter system preferably further includes a fourth electrode group including electrodes provided closer to the proximal side than the second electrode group in the longitudinal direction of the catheter, the fourth electrode group being used to measure the intracardiac potential.

The present invention also includes a defibrillation power supply device to be connected to an electrocardiograph and a catheter having electrodes, and to generate a voltage to be applied to the catheter. The defibrillation power supply device includes a first connecting part to be connected to a 1-1 electrode and a 2-1 electrode of the catheter, the 2-1 electrode being disposed closer to a proximal side than the 1-1 electrode; a second connecting part to be connected to a 1-2 electrode and a 2-2 electrode of the catheter, the 1-2 electrode being disposed closer to the proximal side than the 1-1 electrode and closer to a distal side than the 2-1 electrode, the 2-2 electrode being disposed closer to the proximal side than the 2-1 electrode; a third connecting part to be connected to the electrocardiograph; a first power supply part for generating the voltage to be applied to the 1-1 electrode and the 2-1 electrode; and a second power supply part for generating the voltage to be applied to the 1-2 electrode and the 2-2 electrode. The first connecting part and the second connecting part are connected to the third connecting part without a switching part, the first connecting part is connected to the first power supply part, and the second connecting part is connected to the second power supply part. In the defibrillation power supply device according to the present invention, the first connecting part and the second connecting part are each connected to the third connecting part without a switching part, whereby the first connecting part and the second connecting part are constantly connected to the electrocardiograph. Therefore, the intracardiac potential can be measured by each electrode even during defibrillation.

The present invention also includes a method for controlling a defibrillation power supply device that is connected to an electrocardiograph and a catheter having electrodes, and that generates a voltage to be applied to the catheter. The defibrillation power supply device includes a first power supply part generating the voltage to be applied, a second power supply part generating the voltage to be applied, a first capacitor built in the first power supply part, and a second capacitor built in the second power supply part. The method for controlling the defibrillation power supply device includes charging the first capacitor and the second capacitor with the voltage to be applied while an intracardiac potential is measured by the electrocardiograph. According to the method for controlling, an intracardiac potential having no rounding waveform can be measured independently using each electrode even while the capacitor is being charged.

Advantageous Effects of the Invention

According to the defibrillation catheter system and the defibrillation power supply device of the present invention, the intracardiac potential at each electrode can be measured even during defibrillation. Further, according to the method for controlling the defibrillation power supply device of the present invention, an intracardiac potential having no rounding waveform can be measured independently using each electrode even while the capacitor is being charged.

DESCRIPTION OF EMBODIMENTS

The present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

A defibrillation catheter system according to the present invention includes a catheter extending in a longitudinal direction; a first power supply part for generating a voltage to be applied to the catheter, the first power supply part connected to the catheter; a second power supply part for generating a voltage to be applied to the catheter, the second power supply part connected to the catheter; and an electrocardiograph for measuring an intracardiac potential. The catheter is provided with, on a distal side, a first electrode group having at least a 1-1 electrode and a 1-2 electrode and a second electrode group having at least a 2-1 electrode and a 2-2 electrode, the second electrode group being disposed closer to a proximal side than the first electrode group, the first electrode group and the second electrode group are connected to the electrocardiograph without a switching part, the 1-1 electrode and the 2-1 electrode are connected to the first power supply part, and the 1-2 electrode and the 2-2 electrode are connected to the second power supply part. As described above, in the defibrillation catheter system according to the present invention, the first electrode group and the second electrode group are connected to the electrocardiograph without a switching part, whereby the first electrode group and the second electrode group are constantly connected to the electrocardiograph. Therefore, the intracardiac potential can be measured by each electrode even during defibrillation.

Figure 1:
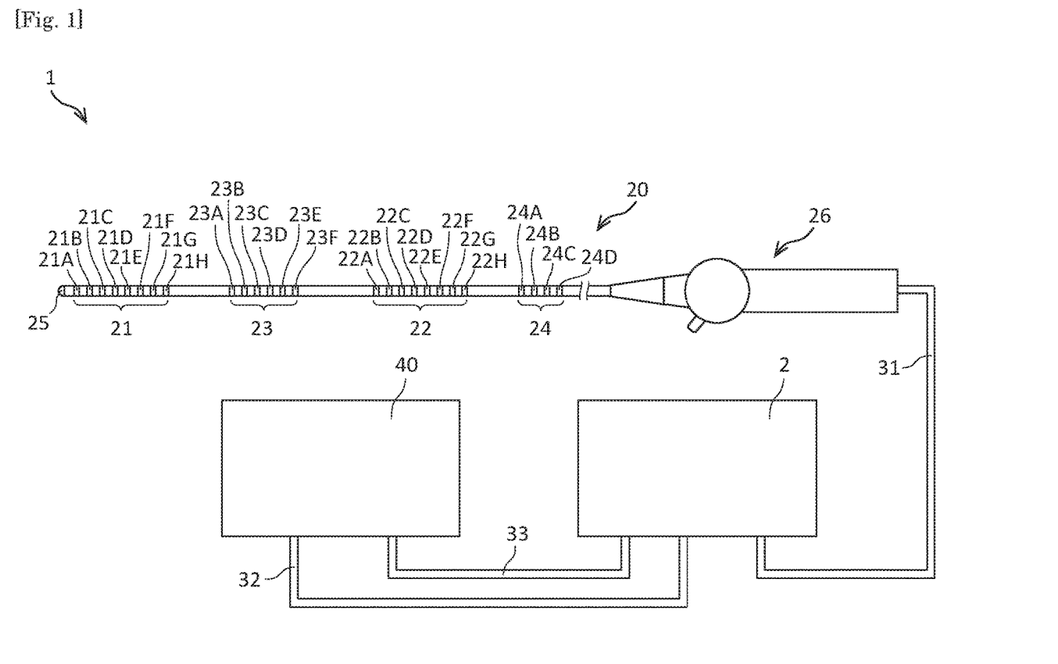
FIG. 1 is a schematic diagram showing a configuration of a defibrillation catheter system according to an embodiment of the present invention.
Figure 2:
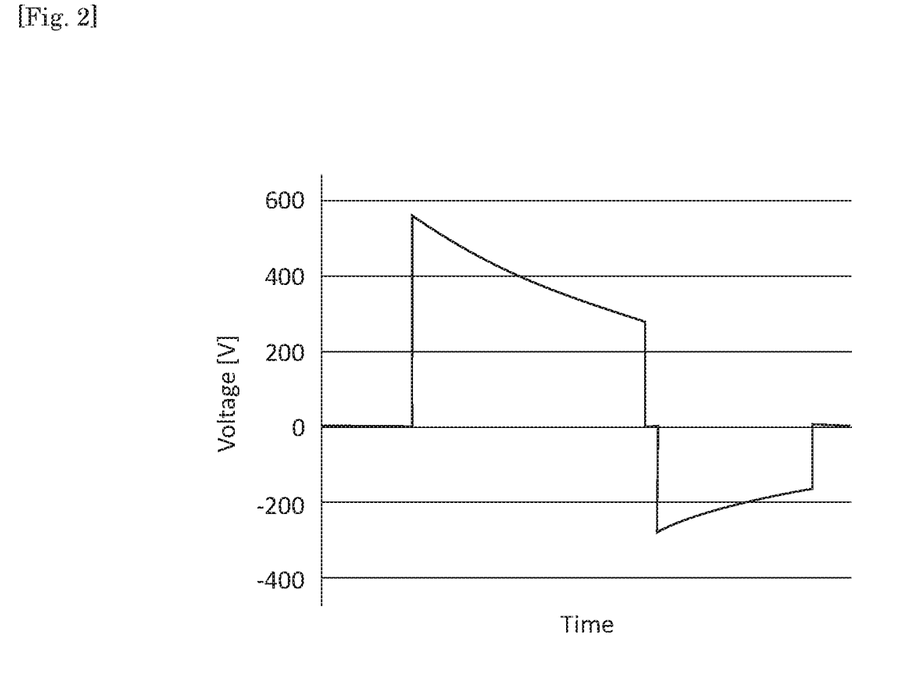
FIG. 2 is a diagram showing an example of a waveform to be applied by a defibrillation catheter system according to the embodiment of the present invention.
Figure 3:
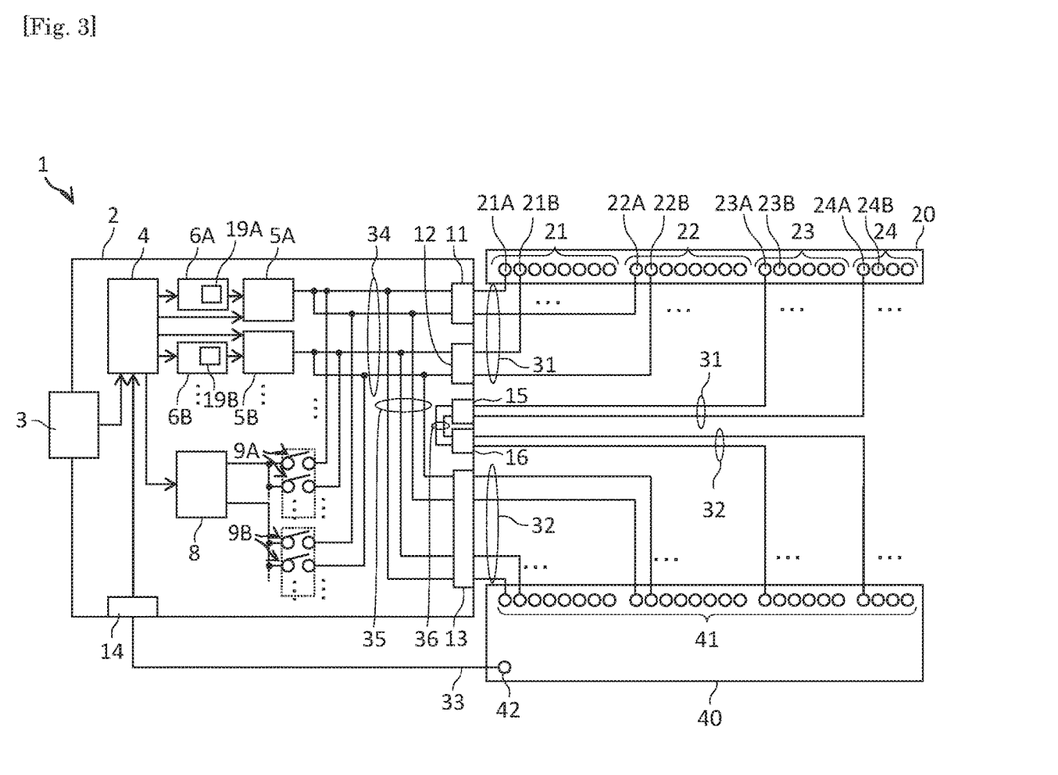
FIG. 3 is a block diagram showing a state of measuring an intracardiac potential and a state of defibrillation by a defibrillation catheter system according to an embodiment of the present invention.
Figure 4:
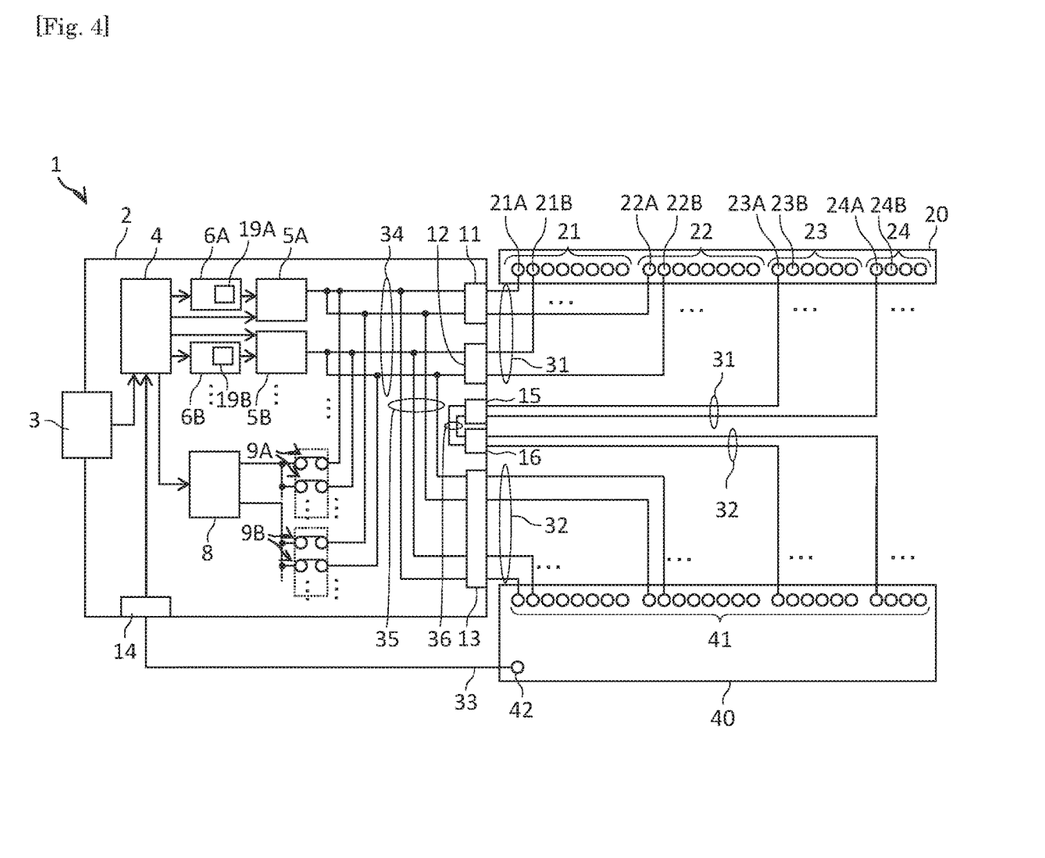
FIG. 4 is a block diagram showing a measurement state of impedance of a defibrillation catheter system according to the embodiment of the present invention.
Figure 5:
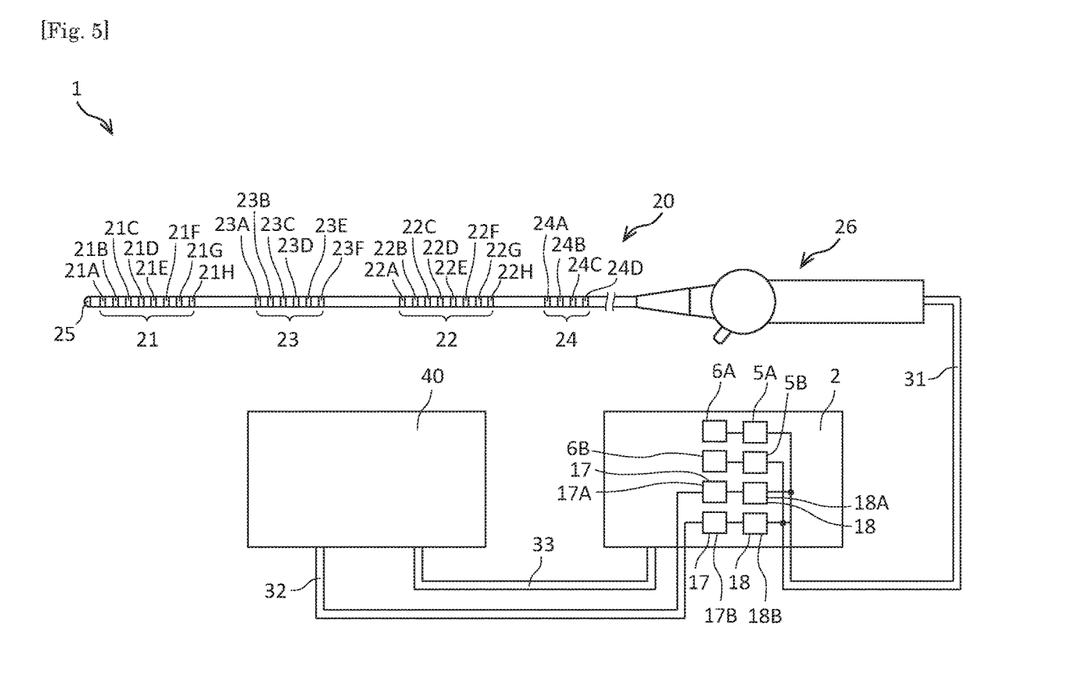
FIG. 5 is a schematic diagram showing another configuration of a defibrillation catheter system according to the embodiment of the present invention.

A defibrillation catheter system 1 and a defibrillation power supply device 2 according to the present invention will be described with reference to FIGS. 1 to 5. FIG. 1 is a schematic diagram showing a configuration of the defibrillation catheter system 1 according to an embodiment of the present invention, and FIG. 2 is a diagram showing an example of a waveform to be applied by the defibrillation catheter system 1 according to the embodiment of the present invention. FIGS. 3 and 4 are block diagrams of the defibrillation catheter system 1 according to the embodiment of the present invention. FIG. 5 is a schematic diagram showing another configuration of a defibrillation catheter system according to the embodiment of the present invention. FIG. 3 shows a state of measuring an intracardiac potential and a state of defibrillation, and FIG. 4 shows a measurement state of impedance. Here, a proximal side of a catheter 20 refers to a direction of a hand side of a user (operator) against an extending direction of the catheter 20, and the distal side refers to an opposite direction to the proximal side (that is, a direction of a treatment target side). In addition, a direction from the proximal side to the distal side of the catheter 20 is referred to as a longitudinal direction.

As shown in FIG. 1, the catheter 20 extends in the longitudinal direction, and provided with a first electrode group 21 and a second electrode group 22 on a distal side thereof. The first electrode group 21 includes at least a 1-1 electrode 21A and a 1-2 electrode 21B. The second electrode group 22 is disposed closer to a proximal side than the first electrode group 21, and includes at least a 2-1 electrode 22A and a 2-2 electrode 22B. When the catheter 20 is inserted into a cardiac cavity, and the first electrode group 21 and the second electrode group 22 are brought into contact with the inner surface of the atrium, ventricle, or blood vessel, the intracardiac potential can be measured using the first electrode group 21 and the second electrode group 22. Moreover, the heart can be stimulated by applying a voltage to the first electrode group 21 and the second electrode group 22. Specifically, a voltage is applied so that a current flows from the first electrode group 21 to the second electrode group 22 via the living body or from the second electrode group 22 to the first electrode group 21 via the living body.

Examples of the catheter 20 include a resin tube formed in a tubular shape. The resin tube can be manufactured by, for example, extrusion molding. Examples of the resin constituting the catheter 20 include polyamide resin, polyester resin, polyurethane resin, polyolefin resin, fluorine resin, vinyl chloride resin, silicone resin, and natural rubber. These materials may be used alone, or two or more of them may be used in combination. Among them, polyamide resin, polyester resin, polyurethane resin, polyolefin resin, and fluorine resin are preferably used.

The catheter 20 may have a single-layer structure or a multi-layer structure. The catheter 20 may be configured such that a part in the longitudinal direction or in the circumferential direction is composed of a single layer, and another part is composed of multiple layers. The catheter 20 may also have one or more lumens.

It is preferable that, when the catheter 20 is inserted into the cardiac cavity, the first electrode group 21 be placed in a position corresponding to the coronary sinus, and the second electrode group 22 be placed in a position corresponding to the right atrium. Due to the first electrode group 21 and the second electrode group 22 being placed as described above, atrial fibrillation can be terminated efficiently.

The first electrode group 21 may have electrodes other than the 1-1 electrode 21A and the 1-2 electrode 21B. For example, in FIG. 1, a 1-3 electrode 21C, a 1-4 electrode 21D, a 1-5 electrode 21E, a 1-6 electrode 21F, a 1-7 electrode 21G, and a 1-8 electrode 21H are provided in order from the distal side as the electrodes constituting the first electrode group 21, in addition to the 1-1 electrode 21A and the 1-2 electrode 21B. Similarly, the second electrode group 22 may have electrodes other than the 2-1 electrode 22A and the 2-2 electrode 22B. For example, in FIG. 1, a 2-3 electrode 22C, a 2-4 electrode 22D, a 2-5 electrode 22E, a 2-6 electrode 22F, a 2-7 electrode 22G, and a 2-8 electrode 22H are provided in order from the distal side as the electrodes constituting the second electrode group 22, in addition to the 2-1 electrode 22A and the 2-2 electrode 22B. When the catheter 20 is provided with many electrodes, intracardiac potentials at various positions can be acquired. For example, the intracardiac potential between the 1-1 electrode 21A and the 1-2 electrode 21B which are adjacent to each other can be measured by measuring the potential difference between the 1-1 electrode 21A and the 1-2 electrode 21B. The same applies to the second electrode group 22. Furthermore, if multiple electrodes are provided, a voltage can be applied to a wide range of the heart, whereby efficient defibrillation can be performed.

To the first electrode group 21 and the second electrode group 22, DC voltages of different polarities are preferably applied. For example, when a biphasic DC voltage as shown in FIG. 2 is applied, fibrillation can be terminated with a small amount of energy. To each of the electrodes 21A to 21H in the first electrode group 21, voltages of the same polarity (positive or negative) are preferably applied, and to each of the electrodes 22A to 22H in the second electrode group 22, voltages of the same polarity (negative or positive) are preferably applied. For example, in the case of applying a biphasic DC voltage as shown in FIG. 2, the first electrode group 21 is negative and the second electrode group 22 is positive in the first half of current application, so that a current flows from the right atrium toward the coronary sinus, and in the latter half of the current application, the first electrode group 21 is positive and the second electrode group 22 is negative, so that a current flows from the coronary sinus toward the right atrium.

It is preferable that the most distal electrode (2-1 electrode 22A in FIG. 1) in the second electrode group 22 be located closer to the proximal side than the most proximal electrode (1-8 electrode 21H in FIG. 1) in the first electrode group 21. Due to such arrangement of the first electrode group 21 and the second electrode group 22, defibrillation can be efficiently performed.

As shown in FIGS. 1 and 3, it is preferable that a third electrode group 23 including electrodes be further provided between the first electrode group 21 and the second electrode group 22 in the longitudinal direction of the catheter 20, the third electrode group 23 being used to measure the intracardiac potential. Due to the third electrode group 23 being provided as described above, the intracardiac potential between the first electrode group 21 and the second electrode group 22 can also be measured. FIG. 1 shows an example in which a 3-1 electrode 23A, a 3-2 electrode 23B, a 3-3 electrode 23C, a 3-4 electrode 23D, a 3-5 electrode 23E, and a 3-6 electrode 23F are provided as the electrodes constituting the third electrode group 23. Note that the third electrode group 23 is preferably not connected to the power supply part. With this configuration, the third electrode group 23 can be used as a dedicated electrode for measuring the intracardiac potential.

As shown in FIGS. 1 and 3, it is preferable that a fourth electrode group 24 including electrodes be further provided closer to the proximal side than the second electrode group 22 in the longitudinal direction of the catheter 20, the fourth electrode group 24 being used to measure the intracardiac potential. Due to the fourth electrode group 24 being provided as described above, the intracardiac potential on a point closer to the proximal side than the second electrode group 22 can be measured. FIG. 1 shows an example in which a 4-1 electrode 24A, a 4-2 electrode 24B, a 4-3 electrode 24C, and a 4-4 electrode 24D are provided as the electrodes constituting the fourth electrode group 24. The fourth electrode group 24 can be disposed at a position corresponding to, for example, the superior vena cava. The fourth electrode group 24 is preferably not connected to the power supply part. With this configuration, the fourth electrode group 24 can be used as a dedicated electrode for measuring the intracardiac potential.

In the following, each of the first electrode group 21, the second electrode group 22, the third electrode group 23, and the fourth electrode group 24 may be collectively referred to as the "each electrode group", and each in the electrode of the first electrode group 21, the electrode of the second electrode group 22, the electrode of the third electrode group 23, and the electrode of the fourth electrode group 24 may be referred to as "each electrode".

The numbers of the electrodes in each electrode group are not particularly limited, and the numbers of the electrodes in each electrode group may be the same or different from each other. Particularly, it is preferable that the number of the electrodes in the first electrode group 21 and the number of the electrodes in the second electrode group 22 be the same. This can easily make the electrodes of the first electrode group 21 and the electrodes of the second electrode group 22 have the same surface area. Due to the configuration in which the electrodes of the first electrode group 21 and the electrodes of the second electrode group 22 have the same surface area, and the electrodes of the first electrode group 21 and the electrodes of the second electrode group 22, the numbers of which are equal, are uniformly arranged, efficient defibrillation can be performed, and the measurement accuracy of intracardiac electrocardiogram can be increased.

The number of the electrodes in the third electrode group 23 is preferably less than or equal to the number of the electrodes in the first electrode group 21, more preferably less than or equal to the number of the electrodes in the first electrode group 21 and less than or equal to the number of the electrodes in the second electrode group 22, and still more preferably less than the number of the number of the electrodes in the first electrode group 21 and less than the number of the electrodes in the second electrode group 22. When the number of the electrodes in the third electrode group 23 is set as described above, the intracardiac potential at each position of the heart can be appropriately measured. For example, the number of the electrodes in the first electrode group 21 and the number of the electrodes in the second electrode group 22 can be set to eight, and the number of the electrodes in the third electrode group 23 can be set to six.

The number of the electrodes in the fourth electrode group 24 is preferably less than or equal to the numbers of the electrodes in the first electrode group 21, less than or equal to the numbers of the electrodes in the second electrode group 22, and less than or equal to the numbers of the electrodes in the third electrode group 23. The number of the electrodes in the fourth electrode group 24 is more preferably less than the numbers of the electrodes in the first electrode group 21, less than the numbers of the electrodes in the second electrode group 22, and less than the numbers of the electrodes in the third electrode group 23. Due to the setting of the number of the electrodes in the fourth electrode group 24 as described above, the potential at the position corresponding to the superior vena cava can be appropriately measured. As shown in FIG. 1, for example, the number of the electrodes in the first electrode group 21 and the number of the electrodes in the second electrode group 22 can be set to eight, the number of the electrodes in the third electrode group 23 can be set to six, and the number of the electrodes in the fourth electrode group 24 can be set to four.

It is preferable that each electrode be present in at least a half region of the outer circumference of the resin tube, and it is more preferable that each electrode be formed in a ring shape. When each electrode is formed in the manner described above, the contact area between each electrode and the heart increases, which facilitates the measurement of intracardiac potential and application of electrical stimulation.

When multiple electrodes are provided, the spacing between adjacent electrodes, that is, the distance between the distal end of one electrode and the proximal end of the other electrode that is located closer to the distal side than one electrode can be set to 1 mm or more and 10 mm or less, and more preferably set to 3 mm or more and 8 mm or less. Further, the width of each electrode can be set to, for example, 0.5 mm or more and 5 mm or less. The electrodes may have the same width or different widths. By setting the distance between the electrodes and the electrode width as described above, the intracardiac potential can be appropriately measured. In order to make the contact conditions with the cardiac muscle equal, it is preferable that the two electrodes for measuring the potential have the same width or the same surface area. The electrode width indicates the length of each electrode in the longitudinal direction.

The distance between the most proximal electrode in the first electrode group 21 and the most distal electrode in the second electrode group 22 is preferably longer than, more preferably five times or more longer than, and still more preferably ten times or more longer than the distance between the electrodes in the first electrode group 21 and the distance between the electrodes in the second electrode group 22. When the distance between the first electrode group 21 and the second electrode group 22 is set as described above, the electrodes are easily placed at predetermined positions of the heart on the basis of the distance. For example, the electrode arrangement and the distance between the electrodes may be set so that the first electrode 21 can be placed in the coronary sinus and the second electrode 22 can be placed in the right atrium. Here, the distance between the electrodes in the first electrode group 21 refers to the longest distance among the distances between two adjacent electrodes of the first electrode group 21. The same applies to the distance between the electrodes in the second electrode group 22.

Each electrode only needs to include a conductive material such as platinum or stainless steel, but preferably contains a radiopaque material such as platinum in order to easily recognize the position of the electrode under X-ray fluoroscopy.

As shown in FIG. 1, a distal tip 25 may be provided at the distal end part of the catheter 20. The distal tip 25 preferably has a tapered portion having an outer diameter which decreases toward the distal side. The distal tip 25 may be made of a conductive material. This allows the distal tip 25 to function as an electrode. Alternatively, the distal tip 25 may be made of a polymer material. Further, the hardness of the distal tip 25 may be set lower than the hardness of the resin tube in order to protect the internal tissues from contacting with the catheter 20.

An operation wire or a spring member for bending the distal side of the catheter 20 may be provided in the lumen of the resin tube. Specifically, it is preferable that the distal end part of the operation wire be fixed to the distal end part of the resin tube or the distal tip 25, and the proximal end part of the operation wire be fixed to a handle 26 described later.

In FIG. 1, a first lead wire 31 is connected to each electrode. Specifically, the inner peripheral surface of each electrode and one end part of the first lead wire 31 disposed in the lumen of the resin tube are joined to each other through a side hole provided in the outer peripheral surface of the resin tube. The other end part of the first lead wire 31 connected to the electrode of the first electrode group 21 or the electrode of the second electrode group 22 is preferably connected to a first connecting part 11 or a second connecting part 12 of the defibrillation power supply device 2 as described later. The other end part of the first lead wire 31 connected to the electrode of the third electrode group 23 or the electrode of the fourth electrode group 24 is preferably connected to a fourth connecting part 14 of the power supply device 2 as described later. The first lead wire 31 may include lead wires connected by a connecting member such as a connector. The same applies to a second lead wire 32 and a third lead wire 33 described later.

The handle 26 gripped by a user during operation of the catheter 20 may be provided on the proximal side of the resin tube. The shape of the handle 26 is not particularly limited, but it is preferable that the handle 26 be formed in a pyramidal shape whose outer diameter decreases toward the distal side in order to relieve stress concentration at the connection portion between the resin tube and the handle 26. The size of the handle 26 is not particularly limited as long as it is suitable for the user to hold with one hand. For example, the length thereof can be set to 5 cm or more and 20 cm or less, and the outermost diameter can be set to 1 cm or more and 5 cm or less. Examples of materials usable for the handle 26 include synthetic resin such as ABS or polycarbonate, and foamed plastic such as polyurethane foam. An opening may be provided in the proximal end part of the handle 26 (more preferably, the proximal end surface of the handle 26), and a part of the first lead wire 31 may extend from the opening, or the first lead wire 31 may be connected to a connector fixed to the opening.

The electrocardiograph 40 measures the intracardiac potential through various electrodes. A known device can be used as the electrocardiograph 40.

FIGS. 1, 3 and 4 show the defibrillation power supply device 2 to be connected to the electrocardiograph 40 and the catheter 20 having electrodes and to generate a voltage to be applied to the catheter. Hereinafter, the defibrillation power supply device may be simply referred to as "power supply device".

The present invention also includes the defibrillation power supply device 2 to be connected to the electrocardiograph 40 and the catheter 20 having electrodes, and to generate a voltage to be applied to the catheter. The defibrillation power supply device 2 includes a first connecting part 11 to be connected to a 1-1 electrode 21A and a 2-1 electrode 22A of the catheter 20, the 2-1 electrode 22A being disposed closer to a proximal side than the 1-1 electrode 21A; a second connecting part 12 to be connected to a 1-2 electrode 21B and a 2-2 electrode 22B of the catheter 20, the 1-2 electrode 21B being disposed closer to the proximal side than the 1-1 electrode 21A and closer to a distal side than the 2-1 electrode 22A, the 2-2 electrode 22B being disposed closer to the proximal side than the 2-1 electrode 22A; a third connecting part 13 to be connected to the electrocardiograph 40; a first power supply part 6A for generating the voltage to be applied to the 1-1 electrode 21A and the 2-1 electrode 22A; and a second power supply part 6B for generating the voltage to be applied to the 1-2 electrode 21B and the 2-2 electrode 22B. The first connecting part 11 and the second connecting part 12 are connected to the third connecting part 13 without a switching part, the first connecting part 11 is connected to the first power supply part 6A, and the second connecting part 12 is connected to the second power supply part 6B. In the defibrillation power supply device 2 according to the present invention, the first connecting part 11 and the second connecting part 12 are each connected to the third connecting part 13 without a switching part, whereby the first connecting part 11 and the second connecting part 12 are constantly connected to the third connecting part 13. Therefore, the intracardiac potential can be measured by each electrode even during defibrillation.

The power supply device 2 is provided with an operation part 3 for performing various operations such as turning on or off the power supply device 2, setting an amount of energy to be applied, performing voltage charging, applying a voltage, and selecting an electrode to which a voltage is to be applied. As the operation part 3, known input means such as a button switch or a lever can be used. The operation part 3 is connected to a control part 4 described later, and an input signal from the operation part 3 is transmitted to the control part 4.

The first power supply part 6A and the second power supply part 6B are connected to the catheter 20 and generate a voltage to be applied. Specifically, the 1-1 electrode 21A and the 2-1 electrode 22A are connected to the first power supply part 6A, and the 1-2 electrode 21B and the 2-2 electrode 22B are connected to the second power supply part 6B. The first power supply part 6A and the second power supply part 6B are each provided with a power supply circuit for generating a DC voltage. The power supply circuit includes, for example, a booster circuit that boosts the DC voltage and a capacitor charged with a voltage to be applied.

In FIG. 3, a first processing part 5A and a second processing part 5B are provided. The first processing part 5A includes an output circuit for outputting a DC voltage to the electrodes from the first power supply part 6A, and the second processing part 5B includes an output circuit for outputting a DC voltage to the electrodes from the second power supply part 6B.

The power supply device 2 is provided with the control part 4 that controls each the power supply part on the basis of an input signal from the operation part 3. The operation part 3 has, for example, a power button for activating the power supply device 2 and an application button that is a defibrillation switch. The control part 4 is connected to the first processing part 5A and the second processing part 5B. In the output circuit of the first processing part 5A, DC voltages having different polarities are applied to the 1-1 electrode 21A and the 2-1 electrode 22A. Similarly, in the output circuit of the second processing part 5B, DC voltages having different polarities are applied to the 1-2 electrode 21B and the 2-2 electrode 22B. The waveform to be applied may be biphasic with reversed polarity, or monophasic with constant polarity, but biphasic waveform is preferable, because it is considered that the biphasic waveform enables stimulation with less energy. The energy to be applied to the living body can be set to, for example, 1 J or more and 30 J or less.

The first electrode group 21 and the second electrode group 22 are connected to the electrocardiograph 40 without the switching part. In other words, the switching part is not provided in the middle of an electric path connecting the first electrode group 21 and the second electrode group 22 to the electrocardiograph 40. Here, the switching part is a section for opening and closing the electric path and switching a direction in which a current flows. Therefore, the electric path from the first electrode group 21 or the second electrode group 22 to the electrocardiograph 40 is not opened or closed, or is not switched, and thus, the first electrode group 21 and the second electrode group 22 are constantly connected to the electrocardiograph 40. Consequently, according to the defibrillation catheter system 1 according to the present invention, the intracardiac potential at each electrode can be measured even during defibrillation.

The first electrode group 21 and the second electrode group 22 are connected to the electrocardiograph 40 without any kinds of switching parts. With this configuration, the first electrode group 21 and the second electrode group 22 can be constantly connected to the electrocardiograph 40.

If an input unit of the electrocardiograph 40 is compatible with a defibrillation-proof applied part, excessive current does not flow from the first power supply part 6A or the second power supply part 6B toward the electrocardiograph 40. Therefore, the first electrode group 21 and the second electrode group 22 may be connected to the electrocardiograph 40 without the switching part. According to JIS T0601-1: 2017, Medical electrical equipment, Part 1: General requirements for basic safety and essential performance, 8.5.5.1 Defibrillation protection, the input of a defibrillation-proof applied part of medical equipment is required to withstand a discharge of 5 kV input through a resistance of 50Ω. The voltage to be applied by the defibrillation catheter system 1 is, for example, at a maximum of 600 V which is sufficiently smaller than 5 kV. Therefore, the electrocardiograph 40 can be sufficiently protected from overvoltage, also due to a resistance of 200Ω or less, more preferably a resistance of 50Ω or more and 200Ω or less being connected between the first electrode 21 and the electrocardiograph 40 and between the second electrode 22 and the electrocardiograph 40 as described later.

As shown in FIG. 5, a resistance 17 of 200Ω or less may be provided at least either one between the first power supply part 6A and the electrocardiograph 40 or between the second power supply part 6B and the electrocardiograph 40. In FIG. 5, a first resistance 17A is provided between the first power supply part 6A and the electrocardiograph 40, and a second resistance 17B is provided between the second power supply part 6B and the electrocardiograph 40. If the resistance 17 is 200Ω or less, the intracardiac potential can be transmitted to the electrocardiograph 40 without rounding the waveform of the intracardiac potential acquired by the catheter 20. The resistance 17 provided between each the power supply part and the electrocardiograph 40 may be 150Ω or less, or 100Ω or less, and may be 50Ω or more, or 70Ω or more.

The number of power supply parts can be set according to the number of electrodes in the first electrode group 21 and the number of electrodes in the second electrode group 22, but preferably, three or more power supply parts including the first power supply part 6A and the second power supply part 6B are provided. As the number of power supply parts is increased, the capacitance of the capacitor can be reduced more, so that the charging time of energy to be delivered can be decreased, and the device can be downsized. However, in order to prevent the power supply device 2 from becoming complicated, the number of power supply parts is preferably ten or less, and more preferably eight or less.

When three or more power supply parts including the first power supply part 6A and the second power supply part 6B are provided, it is preferable that one electrode in the first electrode group 21 and one electrode in the second electrode group 22 be connected to each power supply part, and it is more preferable that one electrode in the first electrode group 21 and one electrode in the second electrode group 22 only be connected to each power supply part. That is, it is preferable that no electrodes other than the 1-1 electrode 21A and the 2-1 electrode 22A be connected to the first power supply part 6A, and no electrodes other than the 1-2 electrode 21B and the 2-2 electrode 22B be connected to the second power supply part 6B. For example, the first power supply part 6A may be connected to the 1-1 electrode 21A and the 2-1 electrode 22A but not to the 1-2 electrode 21B and the 2-2 electrode 22B, and the second power supply part 6B may be connected to the 1-2 electrode 21B and the 2-2 electrode 22B but not to the 1-1 electrode 21A and the 2-1 electrode 22A. When the number of electrodes to be connected to each power supply part is set as described above, it is not necessary to provide a changeover switch for switching between a mode for measuring the intracardiac potential and a mode for applying a voltage between the electrodes and the power supply parts.

It is preferable that the number of power supply parts be equal to the number of electrodes of the first electrode group 21. When the number of power supply parts and the number of electrodes of the first electrode group 21 are set as described above, the electrodes of the first electrode group 21 can each be connected to different power supply parts, whereby there is no need to provide a changeover switch for switching between the mode for measuring intracardiac potential and a mode for applying voltage between the electrodes and the power supply parts. Further, the capacitance of the capacitor can be reduced, whereby the charging time of energy to be delivered can be decreased, and the device can be downsized.

It is preferable that the number of power supply parts be equal to the number of electrodes of the first electrode group 21 and the number of electrodes of the second electrode group 22. With this configuration, each power supply part can be connected to one electrode of the first electrode group 21 and one electrode of the second electrode group 22, whereby there is no need to provide a changeover switch for switching between a mode for measuring the intracardiac potential and a mode for applying a voltage between the electrodes and the power supply parts.

The other end of one first lead wire 31 connected to the 1-1 electrode 21A and the other end of another first lead wire 31 connected to the 2-1 electrode 22A are connected to the first connecting part 11. The first connecting part 11 is connected to the first power supply part 6A through a fourth lead wire 34 and the first processing part 5A. Accordingly, the 1-1 electrode 21A and the 2-1 electrode 22A are connected to the first power supply part 6A, and thus a voltage can be applied. The 1-1 electrode 21A and the 2-1 electrode 22A may be connected to the first power supply part 6A through different connecting members such as a connector.

The other end of one first lead wire 31 connected to the 1-2 electrode 21B and the other end of another first lead wire 31 connected to the 2-2 electrode 22B are connected to the second connecting part 12. The second connecting part 12 is connected to the second power supply part 6B through a fourth lead wire 34 and the second processing part 5B. Accordingly, the 1-2 electrode 21B and the 2-2 electrode 22B are connected to the second power supply part 6B, and thus a voltage can be applied.

In order to facilitate the connection between the power supply device 2 and the catheter 20, it is preferable that the first connecting part 11 have a recess, the other end of the first lead wire 31 be fixed to a first connector having a projection, and the projection of the first connector be engageable with the recess of the first connecting part 11. For the same reason, it is preferable that the second connecting part 12 have a recess, the other end of the first lead wire 31 be fixed to a second connector having a projection, and the projection of the second connector be engageable with the recess of the second connecting part 12.

The other end of the second lead wire 32 connected to an input terminal 41 of the electrocardiograph 40 corresponding to the first electrode group 21 or the second electrode group 22. Further, the third connecting part 13 is connected to the fourth lead wire 34 through a fifth lead wire 35. No switching part is provided on the fourth lead wire 34 and the fifth lead wire 35. Accordingly, the first electrode group 21 and the second electrode group 22 are connected to the electrocardiograph 40 without the switching part, and therefore, the intracardiac potential can be measured through the first electrode group 21 and the second electrode group 22 even during defibrillation. Here, the fourth lead wire 34 and the fifth lead wire 35 may be a wiring material or may be a part of a wiring pattern provided on a printed board. It is preferable that the third connecting part 13 have a recess, the other end of the second lead wire 32 be fixed to a third connector having a projection, and the projection of the third connector be engageable with the recess in the third connecting part 13. This facilitates the connection between the power supply device 2 and the input terminal 41 of the electrocardiograph 40.

The power supply device 2 may include a fourth connecting part 14 that transmits the electrocardiographic waveform output from the electrocardiograph 40 to the control part 4. The third lead wire 33 connected to an output terminal 42 of the electrocardiograph 40 and the control part 4 are connected to the fourth connecting part 14. Thus, the electrocardiographic waveform output from the electrocardiograph 40 can be transmitted to the control part 4, so that the timing of applying the voltage can be controlled so as to be synchronized with the R wave during defibrillation. It is preferable that the fourth connecting part 14 have a recess, the other end of the third lead wire 33 be fixed to a fourth connector having a projection, and the projection of the fourth connector be engageable with the recess in the fourth connecting part 14. This facilitates connection between the power supply device 2 and the output terminal 42 of the electrocardiograph 40.

The power supply device 2 may have a fifth connecting part 15 and a sixth connecting part 16 that connect the electrocardiograph 40 to the third electrode group 23 and the fourth electrode group 24 which are electrodes dedicated to the measurement of the intracardiac potential. The other end of the first lead wire 31 connected to the third electrode group 23 or the fourth electrode group 24 is connected to the fifth connecting part 15. The other end of the second lead wire 32 connected to the input terminal 41 of the electrocardiograph 40 corresponding to the third electrode group 23 or the fourth electrode group 24 is connected to the sixth connecting part 16. The fifth connecting part 15 and the sixth connecting part 16 are connected through a sixth lead wire 36. Here, the sixth lead wire 36 may be a wiring material or a part of a wiring pattern provided on the printed board. For the same reason as the first connecting part 11 to the fourth connecting part 14, it is preferable that the fifth connecting part 15 and the sixth connecting part 16 have recesses, the projection of the first connector be engageable with the recess of the fifth connecting part 15, and the projection of the second connector be engageable with the recess of the sixth connecting part 16.

Examples of the recesses in the first to sixth connecting parts 11 to 16 include a known jack and receptacle, and examples of the projections formed on the first to third connectors include a pin terminal and a plug.

It is preferable that a synchronization circuit for synchronizing timings of applying a voltage to the 1-1 electrode 21A and the 2-1 electrode 22A and applying a voltage to the 1-2 electrode 21B and the 2-2 electrode 22B be connected to the first power supply part 6A and the second power supply part 6B. Due to the synchronization circuit being provided as described above, even if voltages are generated by different power supply parts, timings for applying the voltages to the respective electrodes can be synchronized, which makes it easy to complete the voltage application within the absolute refractory period.

The power supply device 2 may have an electrode selection switch selecting an electrode to which a voltage is applied. With this configuration, electrical stimulation can be applied only to a specific electrode. The position where the electrode selection switch is provided is not particularly limited. However, it is preferable that the electrode selection switch be connected to the first power supply part 6A or the second power supply part 6B, and it is more preferable that the electrode selection switch be provided in the output circuit of the first processing part 5A or the second processing part 5B.

The power supply device 2 may be provided with a safety switch. Due to this configuration, a fail-safe function that can prevent unintended application of voltage to the patient can be provided to the power supply device 2. The safety switch is preferably connected between the control part 4 and the power supply part. The number of safety switches is not particularly limited, but it is preferable that at least one safety switch be provided for the first electrode group 21 and at least one safety switch be provided for the second electrode group 22. In addition, it is preferable that at least one safety switch be provided for the first power supply part 6A and at least one safety switch be provided for the second power supply part 6B.

The power supply device 2 may be provided with a protection circuit that absorbs a high voltage generated when the switch is cut off. This can prevent damage to each switch.

In the present invention, the first electrode group 21 and the second electrode group 22 are connected to the electrocardiograph 40 without the switching part, so that the electrode selection switch and the safety switch are not provided between the electrodes and the electrocardiograph 40.

As shown in FIG. 5, the power supply device 2 may be provided with an overvoltage protection circuit 18 for protecting the electrocardiograph 40 from overvoltage at least either one between the first power supply part 6A and the electrocardiograph 40 or between the second power supply part 6B and the electrocardiograph 40. This configuration can prevent the electrocardiograph 40 from being damaged by the application of overvoltage. In FIG. 5, a first overvoltage protection circuit 18A is provided between the first power supply part 6A and the electrocardiograph 40, and a second over voltage protection circuit 18B is provided between the second power supply part 6B and the electrocardiograph 40.

As shown in FIGS. 3 and 4, it is preferable that an impedance measuring circuit 8 for measuring an impedance between the 1-1 electrode 21A and the 2-1 electrode 22A be connected between the 1-1 electrode 21A and the 2-1 electrode 22A, the 1-1 electrode 21A and the 2-1 electrode 22A be each connected to the impedance measuring circuit 8 through a switch. For example, the 1-1 electrode 21A may be connected to the impedance measuring circuit 8 through a first switch, and the 2-1 electrode 22A may be connected to the impedance measuring circuit 8 through a second switch. With this configuration, the impedance between the first electrode group 21 and the second electrode group 22 can be measured, whereby a waveform to be applied suitable for the patient can be set.

As shown in FIGS. 3 and 4, an impedance measuring circuit 8 for measuring an impedance between the 1-2 electrode 21B and the 2-2 electrode 22B may be connected between the 1-2 electrode 21B and the 2-2 electrode 22B. The impedance measuring circuit 8 may be connected to between the 1-1 electrode 21A and the 2-1 electrode 22A, and between the 1-2 electrode 21B and the 2-2 electrode 22B. In this case, it is preferable that the 1-1 electrode 21A, the 1-2 electrode 21B, the 2-1 electrode 22A, and the 2-2 electrode 22B be each connected to the impedance measuring circuit 8 through a switch. Further, the impedance measuring circuit 8 may be connected to between the first electrode group 21 and the second electrode group 22 through a switch. FIGS. 3 and 4 show an example in which one first switch 9A is provided for each of the 1-1 electrode 21A and the 1-2 electrode 21B in the first electrode group 21, and one second switch 9B is provided for each of the 2-1 electrode 22A and the 2-2 electrode 22B in the second electrode group 22.

The electrode selection switch, the safety switch, the first switch 9A, and the second switch 9B may be of a single-pole single-throw switch or a multi-pole single-throw switch. If each switch is of the single-pole single-throw switch, each switch can be operated individually, which makes it easy to apply a voltage to only a specific electrode. If each switch is of a multi-pole single-throw switch, multiple switches can be activated in conjunction with one another by one operation, so that the accuracy of a timing at which a voltage is applied to each electrode can be enhanced.

Hereinafter, an operation for measuring an intracardiac potential and applying a voltage using the defibrillation catheter system 1 according to the above embodiment will be described. Note that the configurations of the defibrillation catheter system 1 and the defibrillation power supply device 2 are not limited to those in the present embodiment.
(Step 1: Measurement of Intracardiac Potential)

As shown in FIGS. 1 and 3, the power supply device 2, the catheter 20, and the electrocardiograph 40 are connected. The catheter 20 is inserted into the cardiac cavity, and the first electrode group 21 and the second electrode group 22 are placed at the desired locations of the heart. The 1-1 electrode 21A and the 2-1 electrode 22A are connected to the electrocardiograph 40 through the first connecting part 11. The 1-2 electrode 21B and the 2-2 electrode 22B are connected to the electrocardiograph 40 through the second connecting part 12. The potential measured by each electrode is transmitted to the electrocardiograph 40, and the intracardiac electrocardiogram is displayed in the electrocardiograph 40 or a display unit provided separately from the electrocardiograph 40. For early detection of abnormality, it is preferable to start measuring the intracardiac potential in the initial state when the power supply of the power supply device 2 is turned on.
(Step 2: Setting Amount of Energy to be Applied)

An amount of energy to be applied is set using the operation part 3. For example, an arbitrary amount of energy from 1 J to 30 J can be set.
(Step 3: Charging of Energy to be Applied and Measurement of Impedance)

The defibrillation power supply device 2 has a first power supply part 6A and a second power supply part 6B that generate the voltage to be applied, a first capacitor 19A built in the first power supply part 6A, and a second capacitor 19B built in the second power supply part 6B. When the charge button of the operation part 3 is operated, each of the power supply parts charges the capacitor built in each of the power supply parts with a voltage. That is, the method for controlling the power supply device 2 which is connected to the electrocardiograph 40 and the catheter 20 having electrodes, and that generates a voltage to be applied to the catheter 20 according to the present invention preferably includes a charging step for charging the first capacitor 19A and the second capacitor 19B with the voltage to be applied while an intracardiac potential is measured by the electrocardiograph 40. Accordingly, the intracardiac potential having no waveform rounding can be measured independently by each electrode even while the capacitor is being charged. When charging of a voltage corresponding to the amount of energy to be applied set in step 2 is completed, the voltage is maintained. It is preferable that, when the charge button is operated, the impedance between the first electrode group 21 and the second electrode group 22 be measured in parallel with the voltage charging. Specifically, as shown in FIG. 4, all the switches (for example, the first switches 9A and the second switches 9B) are closed, the switches being connected to the impedance measuring circuit 8. As a result, the value of the bioelectrical impedance before current application can be acquired, so that the waveform to be applied can be appropriately set according to the bioelectrical impedance of the patient. The AC voltage applied for measuring the impedance has a frequency and a voltage value enough to calculate the impedance, and the AC voltage only has to be sufficiently lower than the voltage to be applied during defibrillation. During the acquisition of the impedance value, the first switches 9A and the second switches 9B are closed, and the first electrode group 21 and the second electrode group 22 are connected to each other, so that the intracardiac potential waveform obtained by averaging the intracardiac potentials at the respective sites is obtained. Therefore, it is preferable that the measurement time of the impedance be shorter. Preferably, the measurement time is several tens to several hundred of milliseconds. In addition, after the impedance measurement, the first switches 9A and the second switches 9B are opened.

In the defibrillation catheter system 1 according to the present invention, the first electrode group 21 and the second electrode group 22 are connected to the electrocardiograph 40 without a switching part. Therefore, even during charging of energy to be delivered and while the charged voltage is maintained, a local potential at each electrode can be acquired.

(Step 4: Defibrillation)

Returning to FIG. 3 again, when the application button of the operation part 3 is operated, the defibrillation voltage is applied to the patient in synchronization with the R wave of the electrocardiographic waveform input to the fourth connecting part 14 from the electrocardiograph 40. Specifically, the control part 4 selects the waveform to be applied and the energy to be delivered determined in step 3. The first power supply part 6A discharges the first capacitor 19A, and the second power supply part 6B discharges the second capacitor 19B. The first processing part 5A and the second processing part 5B apply a voltage to each electrode so as to generate a biphasic waveform based on the information from the control part 4. The voltage is applied in the absolute refractory period in order to prevent that ventricular fibrillation is caused due to the response of the ventricular muscles. The voltage only has to be applied so as to be synchronized with the R wave of the electrocardiographic waveform from the electrocardiograph 40. The first electrode group 21 and the second electrode group 22 are connected to the electrocardiograph 40 without the switching part. Therefore, the local potentials at the first electrode group 21 and the second electrode group 22 can be continuously measured even during defibrillation, whereby the response of the heart before and after the defibrillation can be observed early.

This application claims the benefit of the priority date of Japanese patent application No. 2018-20530 filed on Feb. 7, 2018. All of the contents of the Japanese patent application No. 2018-20530 filed on Feb. 7, 2018 are incorporated by reference herein.

REFERENCE SIGNS LIST

1: Defibrillation catheter system
2: Defibrillation power supply device (Power supply device)
3: Operation part
4: Control part
5A: First processing part
5B: Second processing part
6A: First power supply part
6B: Second power supply part
8: Impedance measuring circuit
9A: First switch
9B: Second switch
11: First connecting part
12: Second connecting part
13: Third connecting part
14: Fourth connecting part
15: Fifth connecting part
16: Sixth connecting part
17: Resistance
17A: First resistance
17B: Second resistance
18: Overvoltage protection circuit
18A: First overvoltage protection circuit
18B: Second overvoltage protection circuit
19A: First capacitor
19B: Second capacitor
20: Catheter
21: First electrode group
21A: 1-1 electrode
21B: 1-2 electrode
22: Second electrode group
22A: 2-1 electrode
22B: 2-2 electrode
23: Third electrode group
24: Fourth electrode group
25: Distal tip
26: Handle
31: First lead wire
32: Second lead wire
33: Third lead wire
34: Fourth lead wire
35: Fifth lead wire
36: Sixth lead wire
40: Electrocardiograph
41: Input terminal of electrocardiograph
42: Output terminal of electrocardiograph

The invention claimed is:

1. A defibrillation catheter system comprising:
a catheter extending in a longitudinal direction from a distal end to a proximal end;
a first power supply part for generating a voltage to be applied to the catheter, the first power supply part connected to the catheter;
a second power supply part for generating a voltage to be applied to the catheter, the second power supply part connected to the catheter; and
an electrocardiograph for measuring an intracardiac potential, wherein
the catheter is provided with, on a distal side of the catheter, a first electrode group having at least a 1-1 electrode and a 1-2 electrode and a second electrode group having at least a 2-1 electrode and a 2-2 electrode, the second electrode group being disposed closer to a proximal side than the first electrode group,
the first electrode group and the second electrode group are connected to the electrocardiograph without a switching part,
the 1-1 electrode and the 2-1 electrode are connected to the first power supply part, the 1-2 electrode and the 2-2 electrode are connected to the second power supply part, the first power supply part is connected to the 1-1 electrode and the 2-1 electrode but not to the 1-2 electrode and the 2-2 electrode, and the second power supply part is connected to the 1-2 electrode and the 2-2 electrode but not to the 1-1 electrode and the 2-1 electrode.

2. The system according to claim 1, wherein
the system includes three or more power supply parts including the first power supply part and the second power supply part, and the number of the power supply parts is equal to the number of the electrodes in the first electrode group.

3. The system according to claim 1, comprising wherein
the first power supply part, the second power supply part, the 1-1 electrode, the 2-1 electrode, the 1-2 electrode, and the 2-2 electrode are configured so that timings of applying a voltage to the 1-1 electrode and the 2-1 electrode and applying a voltage to the 1-2 electrode and the 2-2 electrode are synchronized.

4. The system according to claim 1, further comprising
a resistance of 200Ω or less, the resistance being provided between the first power supply part and the electrocardiograph and/or between the second power supply part and the electrocardiograph.

5. The system according to claim 1, wherein
the electrocardiograph and at least one of the first power supply part and the second power supply part are configured so that the electrocardiograph is protected from an overvoltage.

6. The system according to claim 1, further comprising,
a first switch connected to the 1-1 electrode; and
a second switch connected to the 2-1 electrode, wherein
the first and second switches, the 1-1 electrode, and the 2-1 electrode are configured to measure an impedance between the 1-1 electrode and the 2-1 electrode.

7. The system according to claim 1, further comprising
a third electrode group including electrodes provided between the first electrode group and the second electrode group in the longitudinal direction of the catheter, the third electrode group being used to measure the intracardiac potential.

8. The system according to claim 1, further comprising
a fourth electrode group including electrodes provided closer to the proximal side than the second electrode group in the longitudinal direction of the catheter, the fourth electrode group being used to measure the intracardiac potential.

9. A defibrillation power supply device to be connected to an electrocardiograph and a catheter having electrodes and extending in a longitudinal direction from a distal end to a proximal end, and to generate a voltage to be applied to the catheter, the defibrillation power supply device comprising:

a first connecting part to be connected to a 1-1 electrode and a 2-1 electrode of the catheter, the 2-1 electrode being disposed proximal to the 1-1 electrode;

a second connecting part to be connected to a 1-2 electrode and a 2-2 electrode of the catheter, the 1-2 electrode being disposed proximal to the 1-1 electrode and distal to the 2-1 electrode, the 2-2 electrode being disposed a proximal to the 2-1 electrode;

a third connecting part to be connected to the electrocardiograph;

a first power supply part for generating the voltage to be applied to the 1-1 electrode and the 2-1 electrode; and a second power supply part for generating the voltage to be applied to the 1-2 electrode and the 2-2 electrode, wherein the first connecting part and the second connecting part are connected to the third connecting part without a switching part, the first connecting part is connected to the first power supply part, and the second connecting part is connected to the second power supply part, the second connecting part is located at a different position from the first connecting part, and the first connecting part and second connecting part are electrically insulated.

* * * * *